United States Patent [19]

Smith

[11] Patent Number: 4,819,660
[45] Date of Patent: Apr. 11, 1989

[54] PROSTHETIC SHAPE SENSOR

[75] Inventor: David M. Smith, Surrey, England

[73] Assignee: University of College london, London, England

[21] Appl. No.: 65,406

[22] Filed: Jun. 23, 1987

[30] Foreign Application Priority Data

Jun. 27, 1986 [GB] United Kingdom ............... 8615749

[51] Int. Cl.$^4$ .............................................. A61B 5/10
[52] U.S. Cl. ..................................... 128/774; 33/515
[58] Field of Search ................... 128/774, 779, 782; 33/511–512, 515; 354/76, 79–81

[56] References Cited

U.S. PATENT DOCUMENTS

| | | | |
|---|---|---|---|
| 4,062,355 | 12/1977 | Kaye | 128/779 |
| 4,538,353 | 9/1985 | Gardner | 33/515 X |
| 4,598,717 | 7/1986 | Pedotti | 128/779 |
| 4,604,807 | 8/1986 | Bock et al. | 33/515 X |
| 4,662,079 | 5/1987 | Graf et al. | 33/515 X |
| 4,670,781 | 6/1987 | Aubert et al. | 128/774 X |

FOREIGN PATENT DOCUMENTS

| | | | |
|---|---|---|---|
| 0140681 | 5/1985 | European Pat. Off. | 128/774 |
| 0217970 | 4/1987 | European Pat. Off. | 128/774 |
| 1564781 | 4/1969 | France | 128/774 |
| 2491323 | 4/1982 | France | 128/774 |
| 0923522 | 5/1982 | U.S.S.R. | 128/774 |

Primary Examiner—Kyle L. Howell
Assistant Examiner—Angela D. Sykes
Attorney, Agent, or Firm—Paul Fields

[57] ABSTRACT

A prosthetic shape sensor comprises a single camera unit and a reflecting surface each mounted on a turntable and arranged opposite each other to define therebetween a space for a stump of a patient. The reflecting surface is shaped to fit between the stump and a leg of the patient. The camera unit includes a light source and the camera unit and the reflecting surface are rotatable together on the turntable through at least 180°. The camera unit can collect a series of silhouette views of the stump upon rotation about the stump.

3 Claims, 3 Drawing Sheets

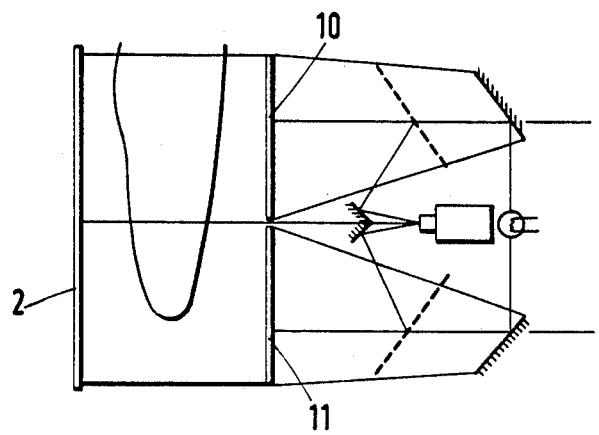
Fig. 4
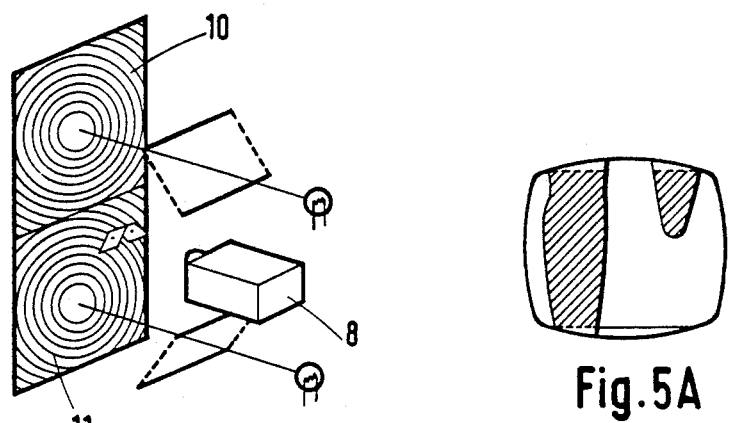
Fig. 5
Fig. 5A
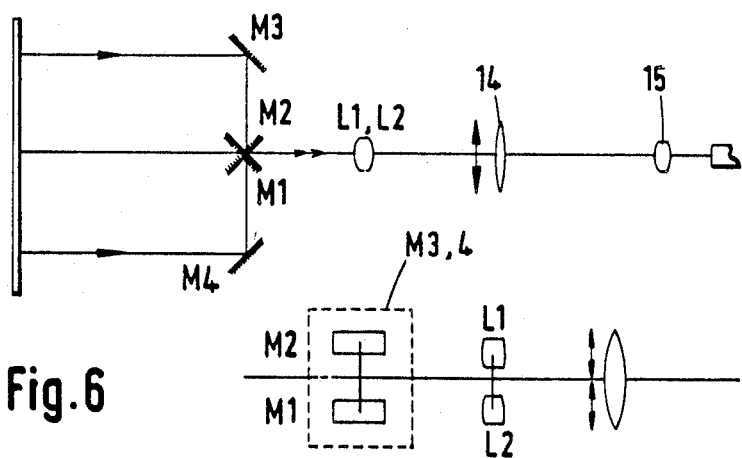
Fig. 6

PROSTHETIC SHAPE SENSOR

FIELD OF THE INVENTION

The present invention relates to a prosthetic sensor, in particular for sensing the shape of belowknee stumps as a preliminary to fabricating prostheses.

PRIOR ART

A shape sensor is known in which a laser beam is directed through a cylindrical lens to form a line of light which is projected onto a stump. When viewed from the side, the line of light is seen to be curved, representing the shape of the stump. The laser line is rotated about the stump and nine cameras are used to record the shape of the line. This sensor is expensive to produce and is rather complicated and bulky.

OBJECT OF THE INVENTION

The present invention aims to provide a shape sensor which is simple, relatively inexpensive and compact.

SUMMARY OF THE INVENTION

According to the invention there is provided a prosthetic shape sensor comprising a single camera unit and a reflecting surface each mounted on a turntable and arranged opposite each other to define therebetween a space for a stump of a patient, the reflecting surface being shaped to fit between the stump and a leg of the patient, wherein the camera unit includes a light source and wherein the camera unit and the reflecting surface are rotatable together on the turntable through at least 180°, whereby the camera unit can collect a series of silhouette views of the stump upon rotation about the stump.

As the unit is rotated a series of clear silhouette views is obtained with no interference from the other leg. From these tangential measures a number of horizontal cross-sections may be calculated to record the stump shape.

BRIEF DESCRIPTION OF THE DRAWINGS

Preferred embodiments of the invention are described in detail below, by example only, with reference to the accompanying drawings, wherein:

FIGS. 2, 3, 4, 5, 5a, and 6 are views showing possible camera and lens configurations.

DESCRIPTION OF THE PREFERRED EMBODIMENTS

Figure 1:
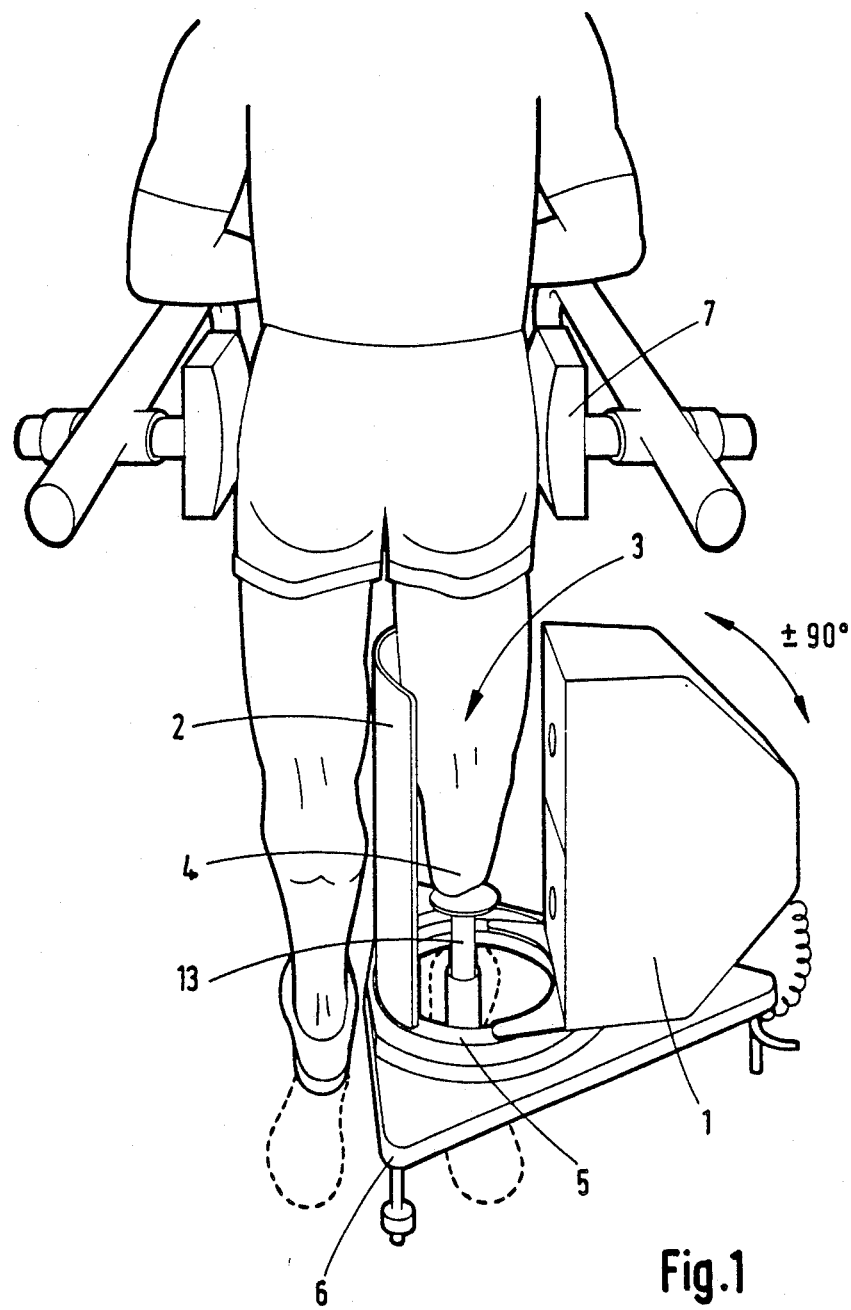
FIG. 1 is perspective view showing the shape sensor, with a patient standing in the space.

As shown in FIG. 1, the shape sensor comprises a single camera unit 1 and a reflecting surface 2. Unit 1 and surface 2 define between them a space 3 for the stump 4 of a patient. The camera unit 1 and surface 2 are mounted together on a turntable 5 which is fitted in a base 6. The turntable 5 can rotate through at least 180° about the stump 4.

As illustrated, the patient can be supported by hip supports 7 and distal rest 13.

Figure 2:
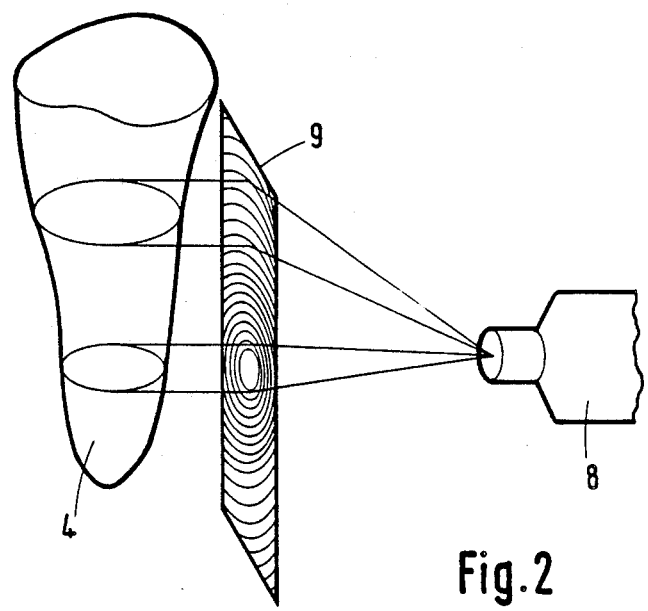

In FIG. 2 is seen camera 8 and a large, therefore fresnel, lens 9 which would be mounted on the front of the camera unit 1. Assuming that the camera diaphragm is at the focal point of the lens 9, all rays transversing the measurement volume, that is stump 4, are parallel. It should be noted that this imaging system is particularly suited to a single camera line illuminated triangulation system, since image deviation across the camera is directly proportional to radius and no geometric corrections are called for in deriving a regular set of data on either axis. While only a single fresnel lens is illustrated, the invention should utilize a double fresnel lens, as explained below.

Figure 3:
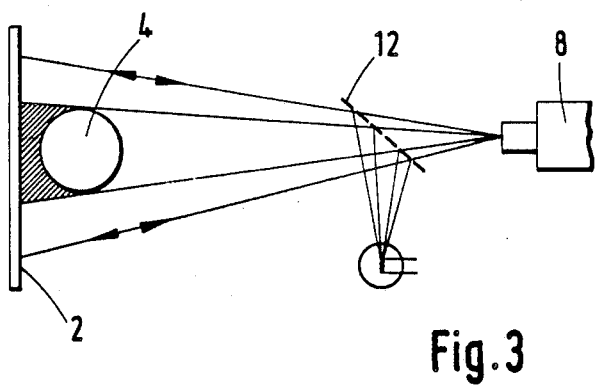

As shown in FIG. 3 illumination for high contrast can be provided by introducing light along the camera axis via a half-silvered mirror 12. The surface 2 is retroreflective, e.g. by being formed from "high gain sheeting" sold by 3M under code T 7610. This allows contrast ratios of 100:1 to be achieved and room lighting could be ignored altogether. With good contrast, simple edge detectors can measure distances along a video line (as in the Vicon system for example, manufactured by Oxford Metrics of Botley, Oxford). This results in low data rates and storage requirements. The screen 2 is thin and curved so as to fit between the knees with minimal interference to the patient's stance.

In practice, it is expected that the measurement volume in the space 3 would not be more than 200 mm in diameter by 500 mm in height. However, this shape does not match the standard video format of 4 by 3. The aspect ratio of the imaged shape could be changed by attaching an anamorphic lens to the camera. However, a single 500 mm high fresnel lens would be costly while reducing the resolving power. Two fresnel lens 10 and 11 are therefore used, one above the other as shown in FIGS. 4 and 5. The camera view is split along two paths by the use of mirrors, and the combined image is shown in FIG. 5A. Alternatively two cameras can be used, keeping each optical system independent.

The camera used could be either a solid state camera or a scanned tube camera. The camera unit can be rotated by hand, which would obviate fears of rogue motor driven devices damaging the stump. With proper support of the stump, it is envisaged that the patient could stand still for 5 seconds. This would allow time for two sweeps of 2 seconds each. The microprocessor receiving the data can compare the results and reject them if there was too great a discrepancy between each sweep.

Another embodiment will now be described which tackles the problem of "keystoning". At the objective lens, the two optical axes enter the lens off its own axis, as they must to split the fields. This results in a situation similar to that of an overhead projector whereby keystoning occurs.

It has been found that tilting the fresnel lenses restores a correct projection of a rectangular image plane to the sensor surface, although some aberration is introduced. In the present embodiment, distortion introduced by off axis working of the fresnel lens are less significant than distortions inherent in the short focal length camera lens.

An alternative method of combining the optical paths without additional aberration is shown in FIG. 6. Mirror pairs M1, M3, and M2, M4 displace the two axes but keep them parallel. Two objective lenses $L_1$, $L_2$ are now used and they form an intermediate image. This is demagnified onto the tube face by a relay lens 15. A field lens 14 is used to maintain pupil imagery.

The above approach is advantageous for another reason. Splitting the field directly with mirrors leads to some overlap. The extent depends on the mirror size and lens aperture. For example if the mirrors were at the lens itself then there would be complete overlap, the two fields simply utilising different parts of the aperture.

The base 6 also allows the introduction of a foot and so that the sensor can be used to record shank shapes to define custom cosmeses, or to record the alignment of successful prostheses while they are worn and load bearing.

What is claimed is:

1. A prosthetic shape sensor comprising a single camera unit and a reflecting surface, each mounted on a turntable and arranged opposite each other to define therebetween a space for a stump of a patient, the reflecting surface being shaped to fit between the stump and a leg of the patient and being formed of retro-reflective material, wherein the camera unit includes a double fresnel lens, means to provide illumination along each axis of said lens, and at least one camera to record the images reflected from the reflecting surface through said lens, and wherein the camera unit and the reflecting surface are rotatable together on the turntable about the stump through at least 180°, whereby the camera unit can collect a series of silhouette views of the stump upon rotation about the stump.

2. A shape sensor according to claim 1, said means to provide illumination comprising a light source, and a series of mirrors for splitting the light from the light source along two paths.

3. A shape sensor according to claim 1, wherein the camera unit comprises a camera for each of said lens.

* * * * *